United States Patent [19]

Imig et al.

[11] 4,145,933

[45] Mar. 27, 1979

[54] FATIGUE FAILURE LOAD INDICATOR

[75] Inventors: Leland A. Imig, Seward, Nebr.; William T. Davis, Yorktown; David C. Davis, Hampton, both of Va.

[73] Assignee: The United States of America as represented by the Administrator of the National Aeronautics and Space Administration, Washington, D.C.

[21] Appl. No.: 889,670

[22] Filed: Mar. 24, 1978

[51] Int. Cl.² ............................................. G01N 3/32
[52] U.S. Cl. ........................................ 73/770; 73/810
[58] Field of Search ...................... 73/91, 92, 90, 770, 73/810

[56] References Cited

U.S. PATENT DOCUMENTS

| 3,304,768 | 2/1967 | Naumann et al. | 73/90 |
| 3,744,300 | 7/1973 | Fleury | 73/91 |

Primary Examiner—Anthony V. Ciarlante
Attorney, Agent, or Firm—William H. King; John R. Manning; Howard J. Osborn

[57] ABSTRACT

An indicator for recording the load at which a fatigue specimen breaks during the last cycle of a fatigue test. A load cell is attached to the specimen which is alternately subjected to tension and compression loads. The output of the load cell which is proportional to the load on the specimen is applied to the input of a peak detector. Each time that the specimen is subjected to a compression load, means are provided for appyling a positive voltage to the reset of the peak detector to reset it. Hence, during the last cycle of the tension load the peak detector measures the maximum load on the specimen. Means are also provided for disconnecting the load cell from the peak detector when there is a failure in the specimen.

4 Claims, 1 Drawing Figure

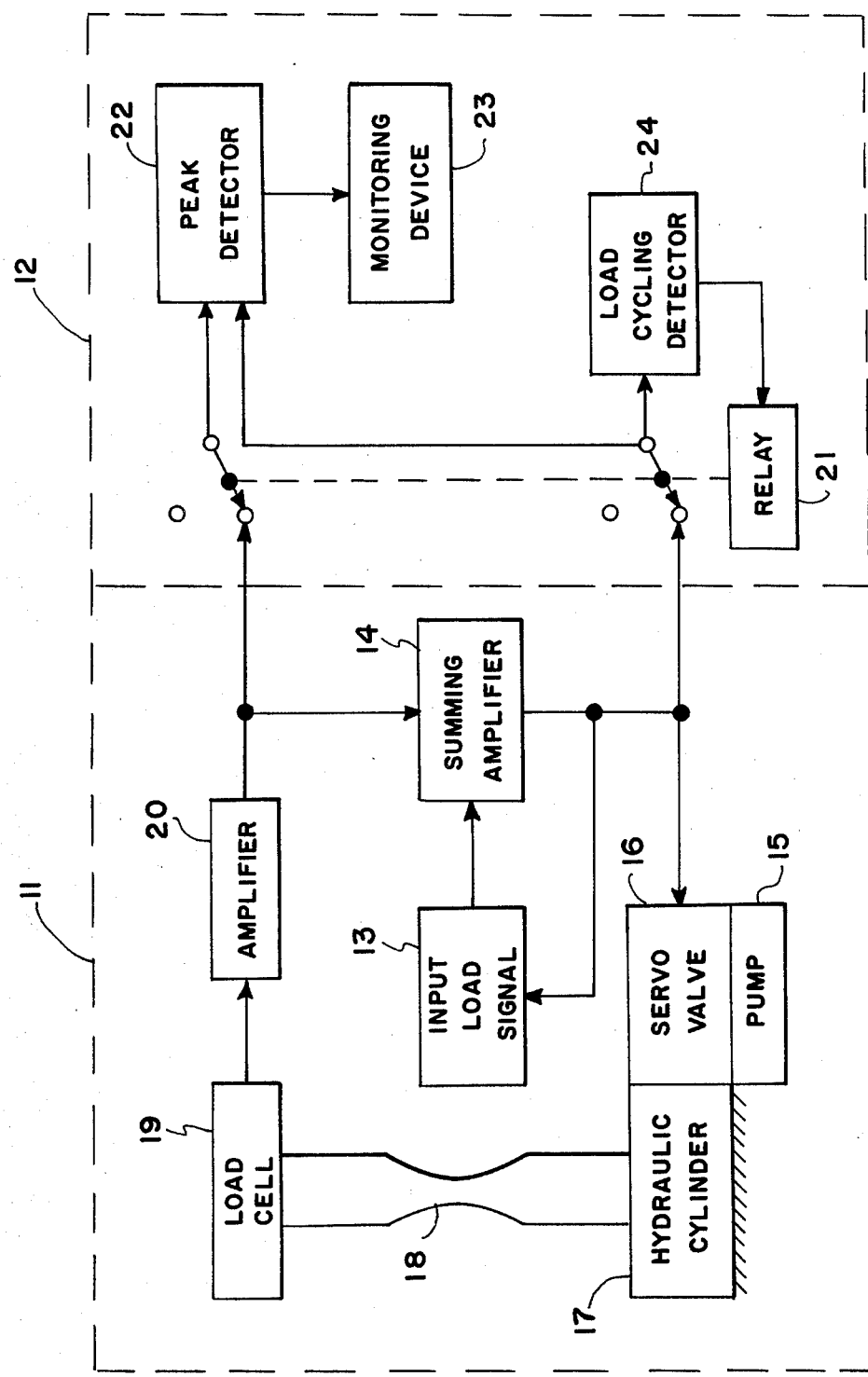

FATIGUE FAILURE LOAD INDICATOR

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

During any fatigue test, loads of controlled magnitudes are applied to a test specimen. The loads may all be the same or they may be of differing amplitudes. At some time during such a test, a fatigue crack will initiate in the specimen and subsequently grow. The larger the fatigue crack becomes the lower the residual strength of the specimen becomes. Finally, the residual strength will be less than that required to resist the current test load, and the specimen will break. The load that causes a specimen to break is generally less than the load control device is attempting to apply to the specimen; but the exact value of the breaking load is unknown.

In a material fatigue test the load usually recorded is the one which the test machine is attempting to apply to the specimen not the actual load at which failure occurs. Hence, this measurement is not the actual failure load. The actual failure load can be determined, but this requires an oscillograph or similar equipment to make continuous load recordings. However, measurements of this type are not practical because of the expense and volume of oscillograph or other recording paper.

It is therefore the primary purpose of this invention to provide a simple and economical means for measuring the load on a test specimen at the instant failure occurs in the specimen.

SUMMARY OF THE INVENTION

A load cell is attached to the specimen under test such that the load cell produces a signal proportional to the load on the specimen. This signal is applied to a peak detector and is disconnected when the specimen fails. Thus, the load value contained in the detector is protected. The system consists of a conventional fatigue testing machine, a peak detector and a load cycling monitor. In operation, the output of the load cell is applied to the peak detector and a summing amplifier. This amplifier combines the load cell signal with the input load control signals to produce an alternating output in phase with load applied to the test specimen. This signal is fed to the load cycling monitor and to the reset terminal of the peak detector so that for each cycle, the peak detector monitors increasing loads and resets during decreasing loads. If the specimen breaks or the cyclic loading is interrupted, the load cycling monitor operates a relay that disconnects the peak detector from the load cell and summing amplifier.

BRIEF DESCRIPTION OF THE DRAWING

The sole FIGURE in this application is a block diagram of the preferred embodiment of the invention.

DETAILED DESCRIPTION OF THE INVENTION

Turning now to the embodiment of the invention selected for illustration in the drawing the number 11 designates a conventional fatigue testing machine. Connected to fatigue testing machine 11 is a fatigue failure load indicator 12 which constitutes this invention.

The fatigue testing machine 11 which is disclosed in detail in U.S. Pat. No. 3,304,768 includes an input load signal device 13 that applies programmed signals to a summing amplifier 14. The output from the summing amplifier 14 is applied to a servo valve 16 which controls the flow of a hydraulic fluid from a pump 15 to a hydraulic cylinder 17 thereby controlling the load applied to a specimen 18. A load cell 19 attached to specimen 18 produces a signal proportional to the load on the specimen. This signal is applied through an amplifier 20 to summing amplifier 14 to subtract from the signal produced by the input load signal device 13 thereby producing a difference error signal at the output of amplifier 14. Hence, each time a different signal is applied from input load signal device 13 to amplifier 14 the load is changed on specimen 18 until the signal at the output of summing amplifier 14 becomes zero. At that time a null detector included with the input load signal device 13 causes the device to apply a different signal to the summing amplifier 14.

In the operation of fatigue testing machine 11 with fatigue failure load indicator 12 the input load signal device 13 is programmed to apply a tension load to the specimen 18 such that while the tension load is being applied the output of summing amplifier 14 is a negative dc signal. When the tension load signal is first applied to amplifier 14 the output of amplifier 14 is a large negative dc signal which decreases as the tension on specimen 18 increases. At the moment the negative dc signal decreases to zero, the null detector causes device 13 to apply a compression load signal or a lower level tension signal to amplifier 14. Consequently, the output of amplifier 14 is a positive dc signal which decreases to zero. At that time another tension load signal is applied by input load signal device 13 to amplifier 14, etc. Thus, the output of amplifier 14 is a series of dc signals alternating from positive to negative and in phase with the input load signals produced by device 13. The output of amplifier 14 is negative while a tension load is being applied to specimen 18 and is positive while a decreasing load is being applied to specimen 18.

The fatigue failure load indicator 12 includes a relay 21, a peak detector 22, a monitoring device 23, and a load cycling detector 24. The output of amplifier 20 which is a dc signal proportional to the load on specimen 18 is applied through a closed contact of relay 21 to peak detector 22. The output of summing amplifier 14 is applied through a closed contact of relay 21 to the reset input of peak detector 22 which resets each time a positive dc voltage is applied to the peak detector. This signal is also applied to a load cycling detector 24 which controls relay 21. The output of peak detector 22 is a dc voltage that is equal to the maximum input applied to the peak detector after it has been reset. This output of peak detector 22 can be read out by a monitoring device 23 which is a dc voltmeter. Load cycling detector 24 is a circuit that holds the contacts of relay 21 closed as long as an alternating voltage is being applied to it. Once the alternating voltage is terminated the load cycling detector 24 will no longer hold the contacts of relay 21 closed. Hence, the relay will open disconnecting the fatigue failure load indicator 12 from the fatigue testing machine 11. Load cycling detector 24 can simply be a capacitor with a bleeding circuit connected to it whereby the capacitor remains charged and holds the relay closed while it is receiving an alternating voltage.

As soon as the alternating voltage terminates the capacitor will no longer hold its charge thereby allowing relay 21 to open.

In the operation of this invention, specimen 18 is placed in the machine 11 where tension and compression (or lower level tension) loads are alternately applied to the specimen by means of the input load signal device 13. As a result an alternating voltage appears at the output of summing amplifier 14 which is applied through the closed contacts of relay 21 to the peak detector 22. Consequently, during tension loads to specimen 18, peak detector 22 measures the load on the specimen and during compression loads or lower level tension loads to the specimen the peak detector is reset. Eventually specimen 18 breaks during a tension load and at that instant the voltage produced at the output of amplifier 20 is measured by peak detector 22. After the break the alternating voltage applied to the load cycling detector terminates thereby causing the contacts of relay 21 to open and disconnect the peak detector from amplifier 20. The reason for disconnecting the peak detector from amplifier 20 is to eliminate any errors that might be caused by transient voltages after the break.

The advantages of this invention over the prior art is that it provides a simple, economical means for measuring the load applied to a specimen at the instant of failure.

What is claimed is:

1. Apparatus for measuring the load applied to a specimen at the instant of failure of the specimen comprising:
    means attached to said specimen for producing a signal proportional to the load on said specimen;
    means for alternately producing tension and decreased tension input load signals;
    means receiving said signal proportional to the load on said specimen and said alternating input load signals for producing a difference error signal;
    means receiving said difference error signal for applying loads to said specimen that tend to reduce said difference error signal to zero whereby said difference error signal is a series of dc signals that are alternately positive and negative and in phase with said input load signals; and
    a peak detector having a measuring input and a reset input with its measuring input connected to receive said signal proportional to the load on said specimen and with its reset input connected to receive said difference error signal whereby said peak detector is reset during decreased tension loads to said specimen and registers the tension load on said specimen when it fractures.

2. Apparatus according to claim 1 including means for monitoring the peak load registered by said peak detector.

3. Apparatus according to claim 1 including means for disconnecting said signal proportional to the load on said specimen and said difference error signal from said peak detector whenever said difference error signal ceases to be alternating signals whereby errors due to transients after fracture of the specimen are eliminated.

4. A method for measuring the load applied to a specimen at the instant of failure of the specimen comprising the steps of:
    producing a signal proportional to the load on said specimen;
    alternately producing tension and decreased tension input load signals;
    subtracting said signal proportional to the load on said specimen from said input load signals to form a difference error signal;
    applying loads to said specimen proportional to said difference error signal so as to tend to reduce said difference error signal to zero whereby said difference error signal is a series of dc signals that are alternately positive and negative and in phase with said input load signals; and
    measuring the peak of said signal proportional to the load on said specimen during each tension input load signal, discarding said measurement in response to said decreased tension input load signals and retaining the measurement only when there is a failure of the specimen.

* * * * *